US00PP09719P

United States Patent [19]

Carruth

[11] Patent Number: Plant 9,719

[45] Date of Patent: Dec. 3, 1996

[54] GRANDIFLORA ROSE PLANT NAMED 'WEKBLAGAB'

[75] Inventor: Thomas F. Carruth, Altadena, Calif.

[73] Assignee: Weeks Wholesale Rose Grower, Inc., Upland, Calif.

[21] Appl. No.: 557,231

[22] Filed: Nov. 14, 1995

[51] Int. Cl.[6] ..... A01H 5/00

[52] U.S. Cl. ..... Plt./15

[58] Field of Search ..... Plt./15, 16, 11

[56] References Cited

U.S. PATENT DOCUMENTS

Plt. 6,953 7/1989 Harkness ..... Plt./24

*Primary Examiner*—Howard J. Locker

*Attorney, Agent, or Firm*—Christie, Parker & Hale, LLP

[57] ABSTRACT

A new variety of grandiflora rose suitable for garden decoration, having flowers of deep golden yellow coloration.

1 Drawing Sheet

BACKGROUND OF THE INVENTION

This invention relates to a new and distinct variety of grandiflora Rose. The varietal denomination of the new variety is 'Wekblagab'. It has as its seed parent the variety known as 'Hartanna' (U.S. Plant Pat. No. 6,953) and an undisseminated seedling as its pollen parent.

SUMMARY OF THE INVENTION

Among the features which distinguish the new variety from other presently available and known commercial rose cultivars are the following combination of characteristics: long lasting flowers having gold coloration, large upright clusters bearing many flowers, dark red new growth and strong plant vigor. 'Wekblagab' may be asexually propagated by cuttings, budding, and grafting.

Asexual reproduction of the new variety by budding as performed in Kern County and Upland, Calif., shows that the foregoing and other distinguishing characteristics come true to form and are established and transmitted through succeeding propagations.

COMPARISON WITH PARENTS

The new rose may be distinguished from its seed parent, 'Hartanna' by the following combination of characteristics: whereas 'Hartanna' bears flowers of a yellow coloration, 'Wekblaga' bears flowers of a darker gold coloration. Whereas the seed parent bears regularly rounded to pyramidal clusters of flowers, the new variety bears clusters with more irregular spacing.

The new variety may be distinguished from its pollen parent, an undisseminated seedling, by the following combination of characteristics: whereas 'Wekblagab' is classified as a Grandiflora bearing many flowers in clusters, the pollen parent is classified as a Hybrid Tea bearing most flowers singly. Whereas the pollen parent bears large flowers of gold with a red-orange under petal, the new variety bears significantly smaller flowers of a more even gold coloration.

BRIEF DESCRIPTION OF THE ILLUSTRATION

The accompanying photograph illustrates the plant in color and shows the flowering thereof from bud to full bloom depicted in color as nearly correct as it is possible to make in a color illustration of the character. Throughout this specification, color values are based upon the Colour Chart of The Royal Horticultural Society of London, England, except where common terms of color definition are employed.

DESCRIPTION OF THE NEW VARIETY

The following description is of rose plants of the new cultivar grown outdoors in Upland, Calif., in the month of August. Phenotypic expression may vary with environmental, cultural and climatic conditions, as well as differences in conditions of light and soil.

Flower

The new variety bears its flowers sometimes singly, but usually in clusters of five or more blooms per stem. Flowers are borne in irregular rounded clusters on strong medium to long stems (about 14 to about 20 cm). Outdoors the plant blooms nearly continuously during the growing season. The flowers have a moderate fruity fragrance.

Bud

The peduncle is of average to long length (about 4 to about 5 cm), and usually erect. The surface is moderately rough, with numerous stipitate glands, and some very small prickles. Peduncle color is between 144A and 146B, sometimes lightly suffused with near 183B.

Before the calyx breaks, the bud is about 1.3 to about 1.8 cm in diameter at the widest point, and about 2.2 to about 2.6 cm long, and pointed to ovoid in shape. The surface of the bud bears some stipitate glands usually with slender foliaceous parts extending beyond the tip of the bud equal to about ½ or more of its length. Bud color is between 144A and 146B.

The inner surface of the sepals is covered with fine wooly tomentum; sepal margins are lined with some stipitate glands and hairs.

As the petals open, the bud is about 1.7 to about 2.2 cm in diameter at the widest point, about 2.5 to about 3.3 cm long, and pointed to ovoid in form. The color of the under surfaces of the newly opened petals is between 25B and 23A. At the point where the petal attaches, there is a zone of near 12A. The color of the upper surfaces of the newly opened petals is between 15A and 17B. There is no zone of a different color where the petal attaches. The bud does open up well and is generally not prevented from opening by cold, hot or dry weather.

Bloom

When fully open, the bloom is small to medium, ranging from about 7 to about 10 cm in diameter. Petalage is double with about 24 to 28 petals and about 1 to 4 petaloids arranged regularly. When partially open, the bloom form is high centered to somewhat globular, and the petals are loosely spiraled to cupped with petal edges slightly rolled outward. When fully open, the bloom form is more flat to cupped, and the petals are more loosely cupped to undulated with petal edges somewhat rolled outward.

Petals

The petals are of heavy substance and moderate thickness, with upper surfaces moderately shiny to satiny and under surfaces slightly satiny. The outer petals are nearly round to broadly obovate in shape with rounded apices. The inner petals are more narrowly obovate in shape with rounded apices.

Newly Opened Flower

The under surface of the outer, intermediate and inner petals is between 23A and 24A. At the point where the petal attaches, there is a zone of near 12B. The upper surface of the outer, intermediate and inner petals is between 15B and 14A.

The general tonality of the newly opened flower is between 15b and 14A.

Three Day Old Flower

The under surface of the outer, intermediate and inner petals is between 20B and 22C. At the point where the petal attaches, there is a zone of near 10B. The upper surface of the outer, intermediate and inner petals is between 16C and 14C.

The general tonality of the three day old flower is between 16C and 14C.

On the spent blooms, the petals usually drop off cleanly.

In September in Upland, Calif., blooms on the bush growing outdoors generally last from four to five or more days. Cut roses from plants grown outdoors kept at normal indoor living temperatures generally last five or more days.

Male Reproductive Organs

Stamens are average in number and are arranged regularly about the pistils; a few are tucked in the calyx. The filaments are of irregular length, most with anthers. The anthers are average size and all open approximately at the same time. Anther color is near 17C when immature and near 164A at maturity. Pollen is moderate to abundant and near 14C in color.

Female Reproductive Organs

Pistils are average in number (approximately 60). The styles are uneven, average to long in length, thin to normal in caliper, and loosely bunched. Stigma color is between 3B and 5C. Style color is between 33A and 34A. Ovaries are usually enclosed in the calyx.

Hips are short in length, flattened to ovoid in form, and near 14B in color when ripened. The hip surface is smooth with thick fleshy walls. Seeds are average in number (approximately 7 to 11), and usually medium in size.

Foliage

The compound leaves are usually comprised of three to five leaflets and are borne abundantly. The leaves are medium size (about 8 to about 10 cm in length and about 6.5 to about 8 cm in width at the widest point), moderately heavy to leathery in texture, and matte to semi-glossy in finish. The leaflets are small to medium (about 3.5 to about 5 cm in length and about 2.5 to about 3.5 cm in width at the widest point), shaped oval to ovate with somewhat acute apices and round to acute bases. Their margins are usually simply serrate.

The upper surface of the mature leaf is between 137A and 139A. The under surface of the mature leaf is between 148C and 139C. The upper surface of the young leaf is between 146A and 139B, usually heavily suffused with between 183A and 187A. The under surface of the young leaf is near 147B, usually heavily suffused with between 183C and 187B.

The rachis is average in caliper and shallowly grooved with many stipitate glands on the edges of the upper side. The under side of the rachis is moderately smooth with few stipitate glands and very small prickles.

The stipules are long in length with narrow to medium width short to medium length straight points that usually turn out at an angle of more than 45 degrees.

The plant displays an above average degree of resistance to powdery mildew and rust as compared to other commercial varieties grown under comparable conditions in Upland, Calif.

Growth

The plant has a bushy upright medium height to tall habit (about 125 to about 130 cm in height and about 85 to about 110 cm spread at the widest point), with full branching. It displays very vigorous growth and the canes are of moderate caliper.

The color of the major stems is near 147C. They bear few large prickles which are moderately long (about 0.8 to about 1 cm). The large prickles are almost straight angles severely downward with a long moderately narrow base; prickle color is near 165A. The major stem bears no small prickles.

The color of the branches is near to between 146B and 138B. They bear several large prickles which are moderately long (about 0.8 to about 1 cm). The large prickles are almost straight angled severely downward with a long moderately narrow base; prickle color is near 160B. The branches bear few small prickles of similar shape and coloration.

The color of the new shoots is between 144B and 146B often heavily suffused with between 187A and 183A. They bear many large prickles which are moderately long (about 0.8 to about 1 cm). The large prickles are almost straight angled severely downward with a very long moderately narrow base; prickle color is near 180A. The shoots bear some small prickles of similar shape and coloration.

I claim:

1. A new and distinct variety of grandiflora rose plant substantially as described and illustrated herein.

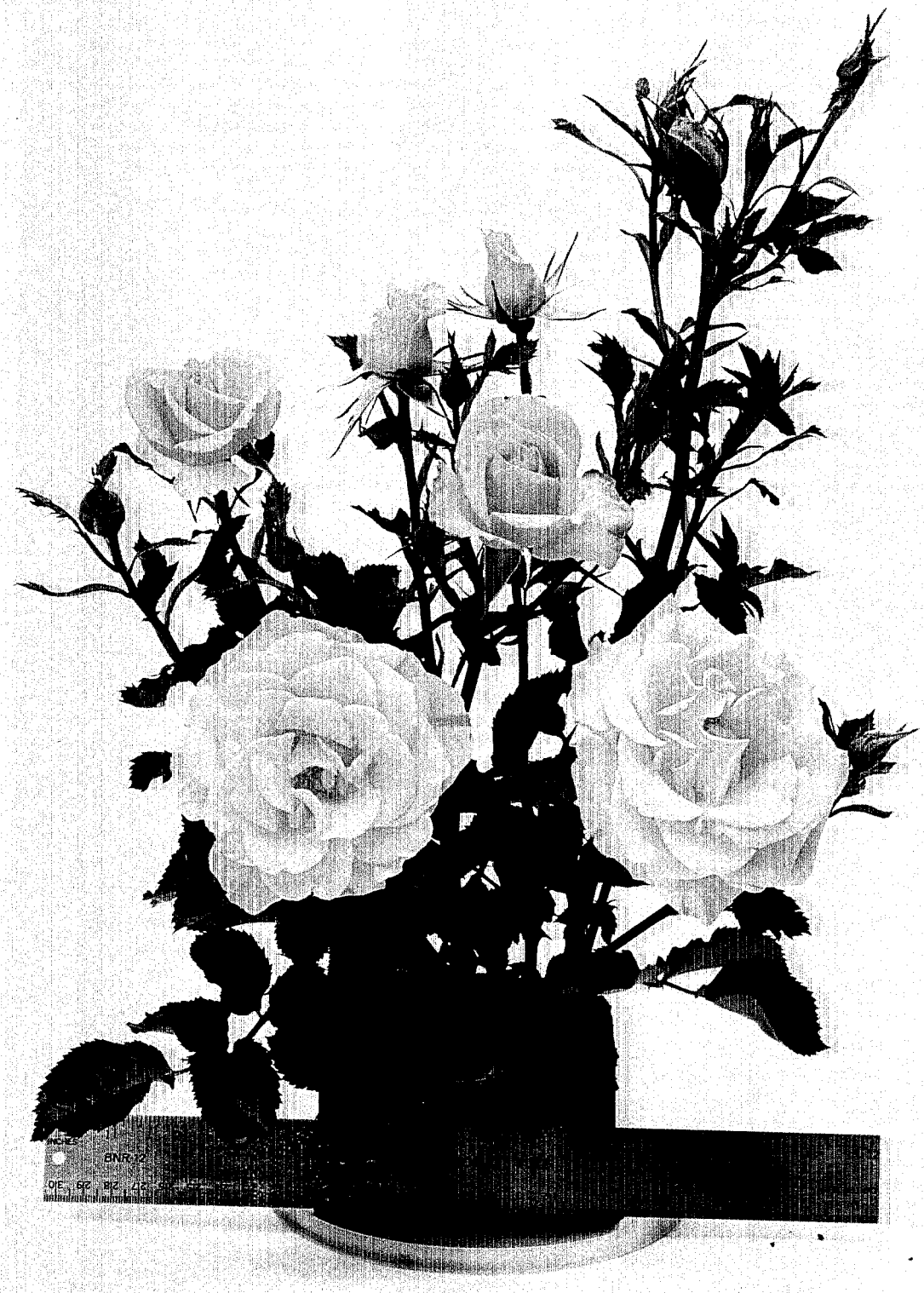

* * * * *